(12) United States Patent
Iwasaki

(10) Patent No.: US 10,888,276 B2
(45) Date of Patent: Jan. 12, 2021

(54) LIVING BODY-ATTACHABLE ELECTRODE

(71) Applicant: Murata Manufacturing Co., Ltd., Kyoto (JP)

(72) Inventor: Kazuki Iwasaki, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 16/809,849

(22) Filed: Mar. 5, 2020

(65) Prior Publication Data

US 2020/0196950 A1 Jun. 25, 2020

Related U.S. Application Data

(63) Continuation of application No. PCT/JP2018/033263, filed on Sep. 7, 2018.

(30) Foreign Application Priority Data

Sep. 8, 2017 (JP) ................. 2017-172893

(51) Int. Cl.
*A61B 5/00* (2006.01)
*H05K 1/11* (2006.01)
*A61B 5/053* (2006.01)

(52) U.S. Cl.
CPC ............ *A61B 5/6832* (2013.01); *H05K 1/115* (2013.01); *A61B 5/053* (2013.01);
(Continued)

(58) Field of Classification Search
CPC .......... A61B 5/6832; A61B 2562/0217; A61B 5/053; A61B 5/00; A61B 2562/125; H05K 1/115; H05K 2201/0314; H05K 1/11
(Continued)

(56) References Cited

U.S. PATENT DOCUMENTS

| 5,928,142 A | 7/1999 | Cartmell et al. |
| 6,434,410 B1 | 8/2002 | Cordero et al. |

(Continued)

FOREIGN PATENT DOCUMENTS

| JP | 2002-85364 A | 3/2002 |
| JP | 2002-518076 A | 6/2002 |
| JP | 2015-521085 A | 7/2015 |

OTHER PUBLICATIONS

International Search Report for International Application No. PCT/JP2018/033263, dated Nov. 20, 2018.
(Continued)

*Primary Examiner* — Tremesha S Willis
(74) *Attorney, Agent, or Firm* — Pearne & Gordon LLP

(57) ABSTRACT

A living body-attachable electrode includes a substrate that has a first main surface and a second main surface and is made of a material having stretchability, a first electrode pair that is formed on/in the first main surface and includes two opposite electrodes, a second electrode pair that is formed on/in the first main surface and includes two opposite electrodes sandwiching the first electrode pair, and a plurality of gel electrodes that are formed on the second main surface and are in a one-to-one correspondence with the electrodes in the first and second electrode pairs. Each of the electrodes in the first and second electrode pairs and corresponding one of the gel electrodes are electrically connected to each other via a plurality of via conductors penetrating through the substrate.

10 Claims, 14 Drawing Sheets

(52) U.S. Cl.
CPC .. *A61B 2562/0217* (2017.08); *A61B 2562/125* (2013.01); *H05K 2201/0314* (2013.01)

(58) Field of Classification Search
USPC ........................................................ 174/262
See application file for complete search history.

(56) References Cited

U.S. PATENT DOCUMENTS

| | | |
|---|---|---|
| 2003/0176808 A1 | 9/2003 | Masuo |
| 2004/0181141 A1 | 9/2004 | Kislov et al. |
| 2013/0325096 A1 | 12/2013 | Dupelle et al. |
| 2018/0020977 A1* | 1/2018 | Li ........................ A61B 5/002 600/384 |

OTHER PUBLICATIONS

Written Opinion for International Application No. PCT/JP2018/033263, dated Nov. 20, 2018.

* cited by examiner

| R | 0 | 2 | w/2(=4mm) |
|---|---|---|---|
| MAXIMUM STRESS (Mpa) | 1.675 | 1.481 | 1.365 |

FIG. 10

| MEASURING ELECTRODE | | LINEAR SHAPE (A) | BRACKET SHAPE (B) | ARC SHAPE (C) |
|---|---|---|---|---|
| Y DIRECTION | | | | |
| X DIRECTION | | | | |
| OBLIQUE DIRECTION | | | | |
| MAXIMUM STRESS VALUE [Pa] | Y DIRECTION | 611k | 577k | 557k |
| | X DIRECTION | 537k | 577k | 535k |
| | OBLIQUE DIRECTION | 1.36M | 1.28M | 1.25M |

LIVING BODY-ATTACHABLE ELECTRODE

This is a continuation of International Application No. PCT/JP2018/033263 filed on Sep. 7, 2018 which claims priority from Japanese Patent Application No. 2017-172893 filed on Sep. 8, 2017. The contents of these applications are incorporated herein by reference in their entireties.

BACKGROUND

Technical Field

The present disclosure relates to an electrode that is attached to a human body to detect a biological signal.

The management of the state of a human body has been recently performed by acquiring biological information and analyzing the biological information. In particular, the detection of a foreign body in a human body is needed. The detection of a foreign body in a human body is performed by bioimpedance measurement.

Patent Document 1 discloses an electrophysiological signal measurement electrode in which a barrier layer made of a conductive material is disposed between a print wiring line and liquid electrolytic gel on a flexible substrate. The disposition of the barrier layer realizes the longer shelf life of the electrophysiological signal measurement electrode and the maintenance of acceptable impedance when the electrophysiological signal measurement electrode is used.

Patent Document 1: Japanese Unexamined Patent Application Publication (Translation of PCT Application) No. 2002-518076

BRIEF SUMMARY

As disclosed in Patent Document 1, the print wiring line and the liquid electrolytic gel are electrically connected to each other by a metal hook. When the metal hook that is hard is attached to a human body, the burden to the human body is great. A stress easily occurs because of the movement of the human body. The interface resistance between the print wiring line and the liquid electrolytic gel easily changes. Measurement noises are therefore easily generated.

The present disclosure provides a living body-attachable electrode with which the burden to a human body is suppressed when the living body-attachable electrode is attached to a living body and high measurement accuracy is realized.

A living body-attachable electrode according to an embodiment of the present disclosure includes a substrate that has a first main surface and a second main surface and is made of a material having stretchability, a first electrode pair that is formed on/in the first main surface and includes two opposite electrodes, a second electrode pair that is formed on/in the first main surface and includes two opposite electrodes sandwiching the first electrode pair, and a plurality of gel electrodes that are formed on the second main surface and are in a one-to-one correspondence with the electrodes in the first and second electrode pairs. Each of the electrodes and corresponding one of the gel electrodes are electrically connected to each other via a plurality of via conductors penetrating through the substrate.

According to the present disclosure, there can be provided a living body-attachable electrode with which the burden to a human body is suppressed when the living body-attachable electrode is attached to a living body and high measurement accuracy is realized.

BRIEF DESCRIPTION OF THE SEVERAL VIEWS OF THE DRAWINGS

FIG. 10 is a diagram illustrating stress measurement results corresponding to measuring electrodes of various shapes.

DETAILED DESCRIPTION

An embodiment of the present disclosure will be described in detail below with reference to the accompanying drawings.

1. Configuration of Living Body-Attachable Electrode

Figure 1:
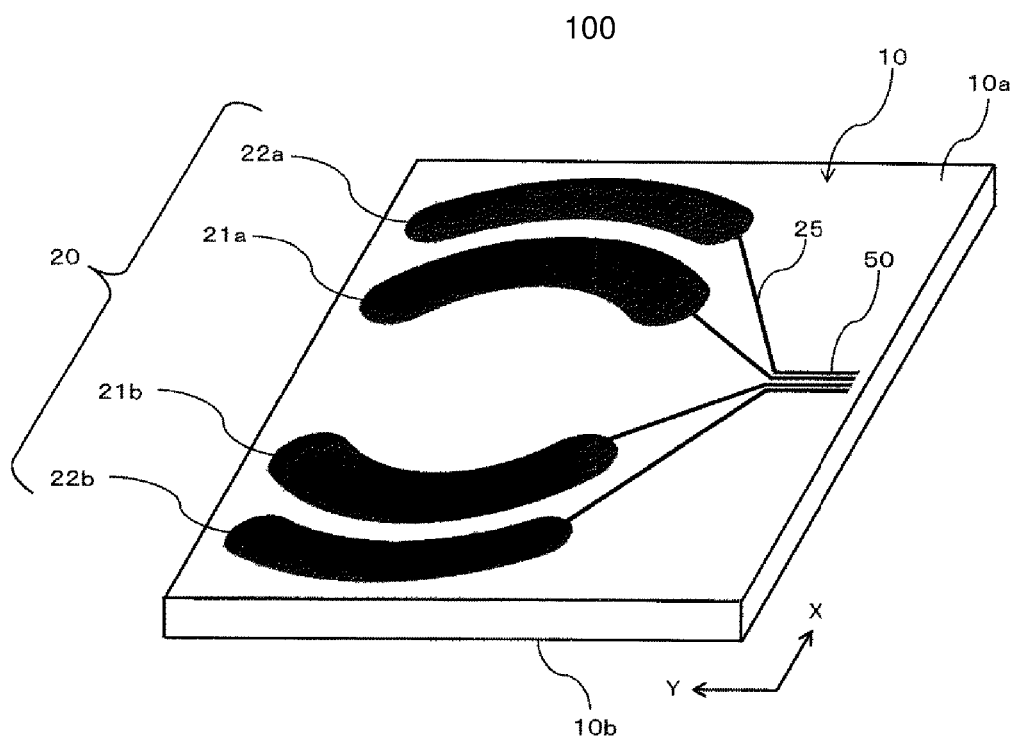
FIG. 1 is the perspective view of a living body-attachable electrode according to an embodiment of the present disclosure.
Figure 2A:
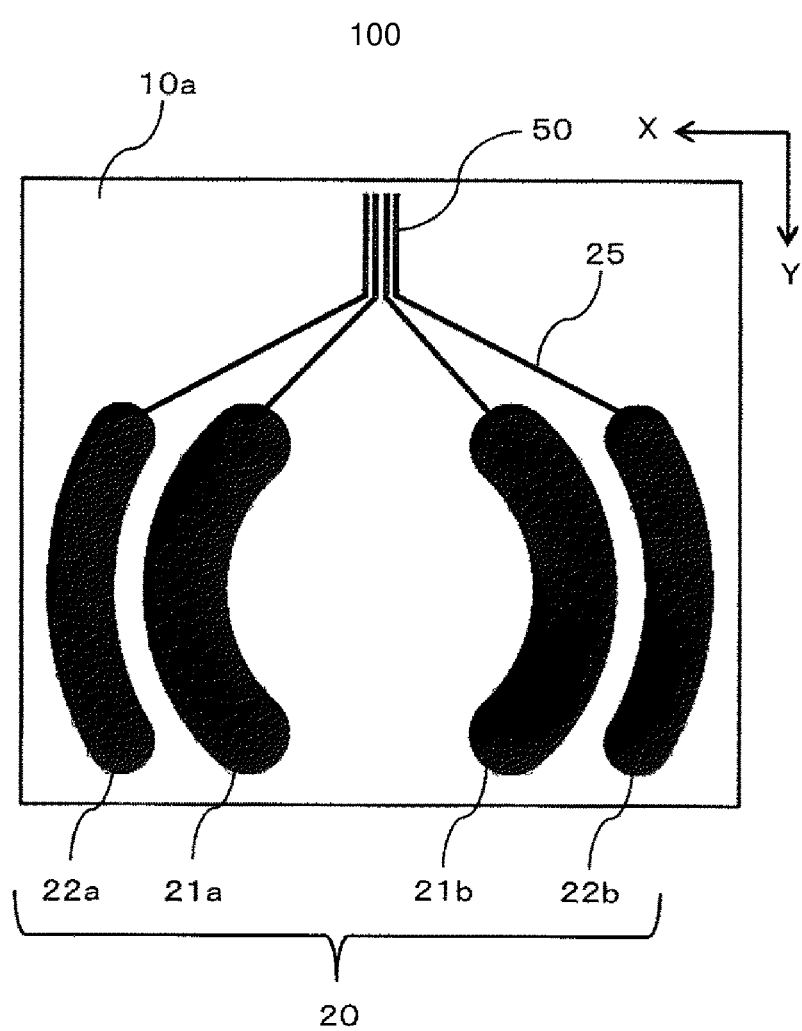
FIG. 2A is the plan view of a living body-attachable electrode.

A living body-attachable electrode to be described below is an electrode that is attached to a part of a living body (for example, a human body) to measure a biological signal. FIG. 1 is the perspective view of a living body-attachable electrode according to an embodiment of the present disclosure. FIG. 2A is the plan view of a living body-attachable electrode.

As illustrated in these drawings, a living body-attachable electrode 100 includes a substrate 10 made of a material having stretchability, measuring electrodes 21a, 21b, 22a, and 22b for measuring the electric signal of a living body, and a connector pad 50 for transmitting a measured electric signal to an external apparatus.

The substrate 10 is made of a resin material having stretchability such as thermoplastic polyurethane. The substrate 10 has a first main surface 10a and a second main surface 10b. On the side of the first main surface 10a of the substrate 10, a plurality of measuring electrodes 20 are formed.

The measuring electrodes 21a, 21b, 22a, and 22b are used in four-terminal sensing measurement. The measuring electrodes 21a and 21b are a pair of electrodes for voltage measurement. The measuring electrodes 22a and 22b are a pair of electrodes for the application of a current. The measuring electrodes 21a and 21b are disposed to face each other. The measuring electrodes 22a and 22b are disposed such that they face each other to sandwich the measuring electrodes 21a and 21b. The measuring electrodes 21a and 22a and the measuring electrodes 21b and 22b facing the measuring electrodes 21a and 22a are arranged symmetrically about a reference line connecting midpoints between opposite electrodes. Each of the measuring electrodes 21a, 21b, 22a, and 22b is connected to the connector pad 50 via a lead wiring line 25. The lead wiring lines 25 connected to the measuring electrodes 21a and 22a and the lead wiring lines 25 connected to the measuring electrodes 21b and 22b are also arranged symmetrically about the above reference line. By symmetrically arranging the measuring electrodes 21a, 21b, 22a, and 22b and the lead wiring lines 25 as described above, noises generated between the connector pad 50 and respective via electrodes (to be described below) are likely to be equal. The calibration at the subsequent stage can therefore be easily performed.

Figure 2B:
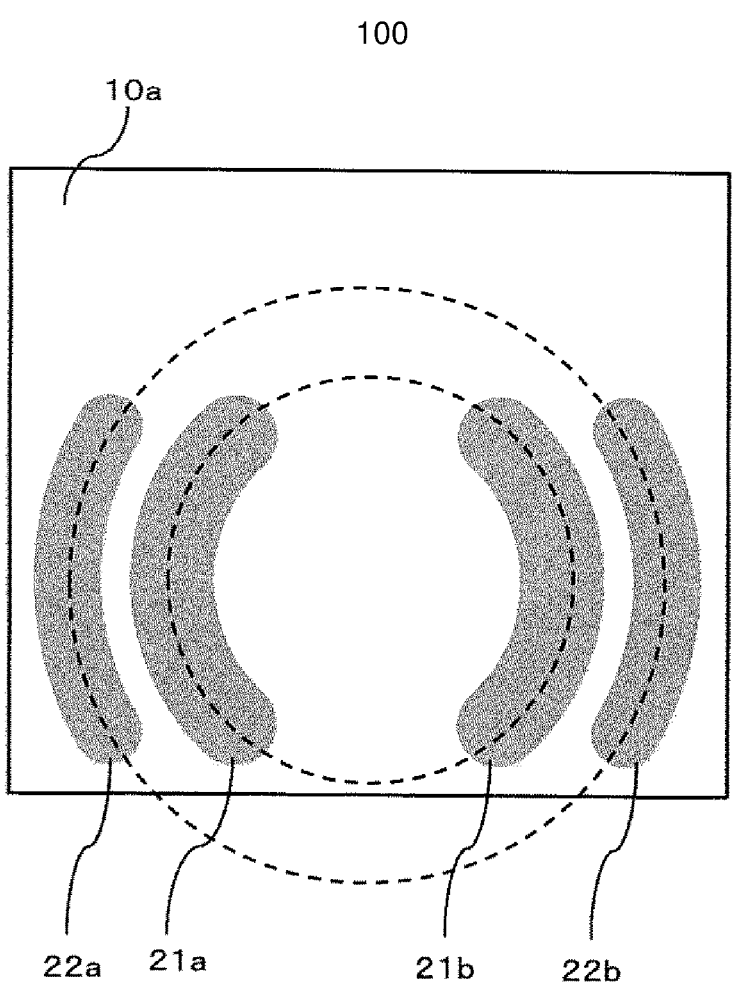
FIG. 2B is a diagram describing concentrically arranged measuring electrodes.

The measuring electrodes 22a and 22b used for the application of a current are disposed outside the measuring electrodes 21a and 21b used for voltage measurement, respectively. Each of the measuring electrodes 21a, 21b, 22a, and 22b has an arc shape. The arc shape can scatter the stress that occurs at the living body-attachable electrode 100 because of the movement of a human body. As illustrated in FIG. 2B, the measuring electrodes 21a and 21b are on the same circumference and are located at the respective positions of a pair of arcs facing each other across the center of a circle. The measuring electrodes 22a and 22b are similarly on the same circumference and are located at the respective positions of a pair of arcs facing each other across the center of a circle. The measuring electrodes 21a and 21b used for voltage measurement are concentrically disposed and the measuring electrodes 22a and 22b used for the application of a current are concentrically disposed (see FIG. 2B).

Specifically, the thickness of the substrate 10 is, for example, 40 μm. Each of the measuring electrodes 21a and 21b placed on the inner side has the arc shape with the width of 8 mm, the radius of 19 mm, and the angle of 95°. Each of the measuring electrodes 22a and 22b placed on the outer side has the arc shape with the width of 6.4 mm, the radius of 29.2 mm, and the angle of 61°. The larger the areas of the measuring electrodes 21a and 21b, the larger the amount of reduction in interface resistance becomes and the higher the measurement accuracy becomes. It is therefore desirable that the areas of the measuring electrodes 21a and 21b be larger than those of the measuring electrodes 22a and 22b.

In the following description, as illustrated in FIG. 1, the direction from the measuring electrode 22b to the measuring electrode 22a is defined as an X direction (lateral direction) and a direction orthogonal to this direction is defined as a Y direction (vertical direction).

Figure 2C:
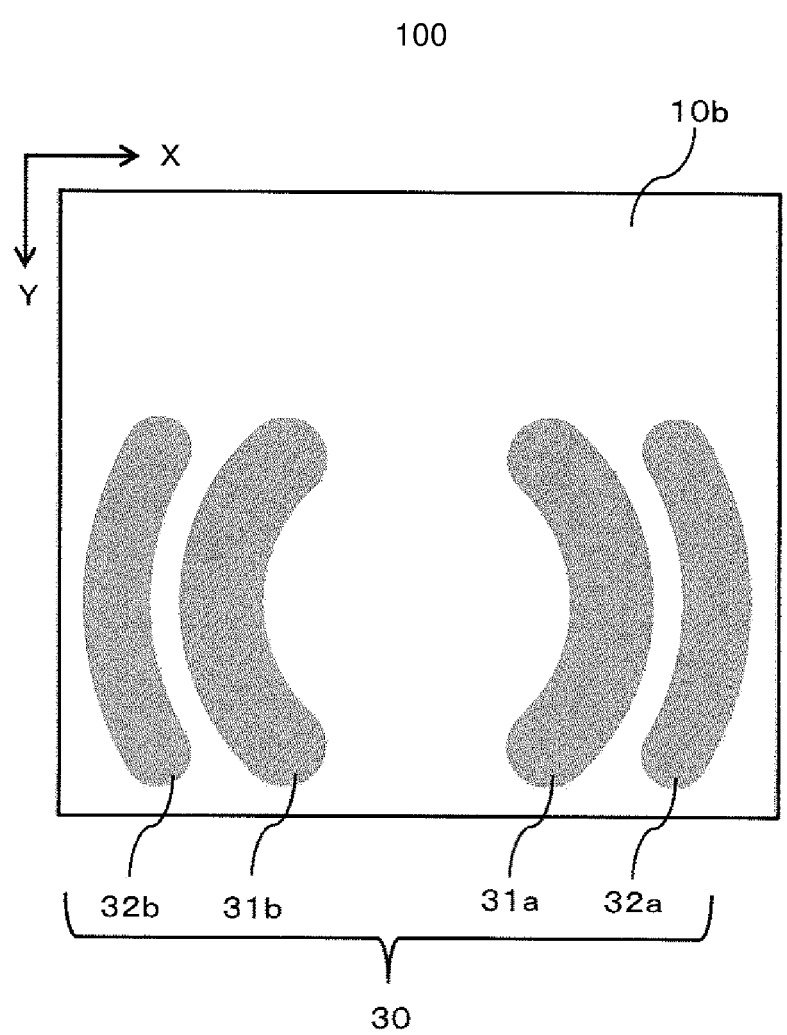
FIG. 2C is the bottom view of a living body-attachable electrode.

FIG. 2C is the bottom view of the living body-attachable electrode 100 viewed from the second main surface 10b. As illustrated in FIG. 2C, in the living body-attachable electrode 100, gel electrodes 31a, 31b, 32a, and 32b (hereinafter also collectively referred to as a "gel electrode 30") are further formed on the second main surface 10b of the substrate 10. Each of the gel electrodes 31a, 31b, 32a, and 32b is made of a conductive gel material containing water, a moisturizing agent, and an electrolyte. On the second main surface 10b, the gel electrodes 31a, 31b, 32a, and 32b are disposed opposite the measuring electrodes 21a, 21b, 22a, and 22b formed on/in the first main surface 10a, respectively such that they are electrically connected to the measuring electrodes 21a, 21b, 22a, and 22b, respectively. The gel electrodes 31a, 31b, 32a, and 32b have the same shapes as the measuring electrodes 21a, 21b, 22a, and 22b, respectively. That is, the gel electrodes 31a, 31b, 32a, and 32b also have the arc shape.

Figure 3:
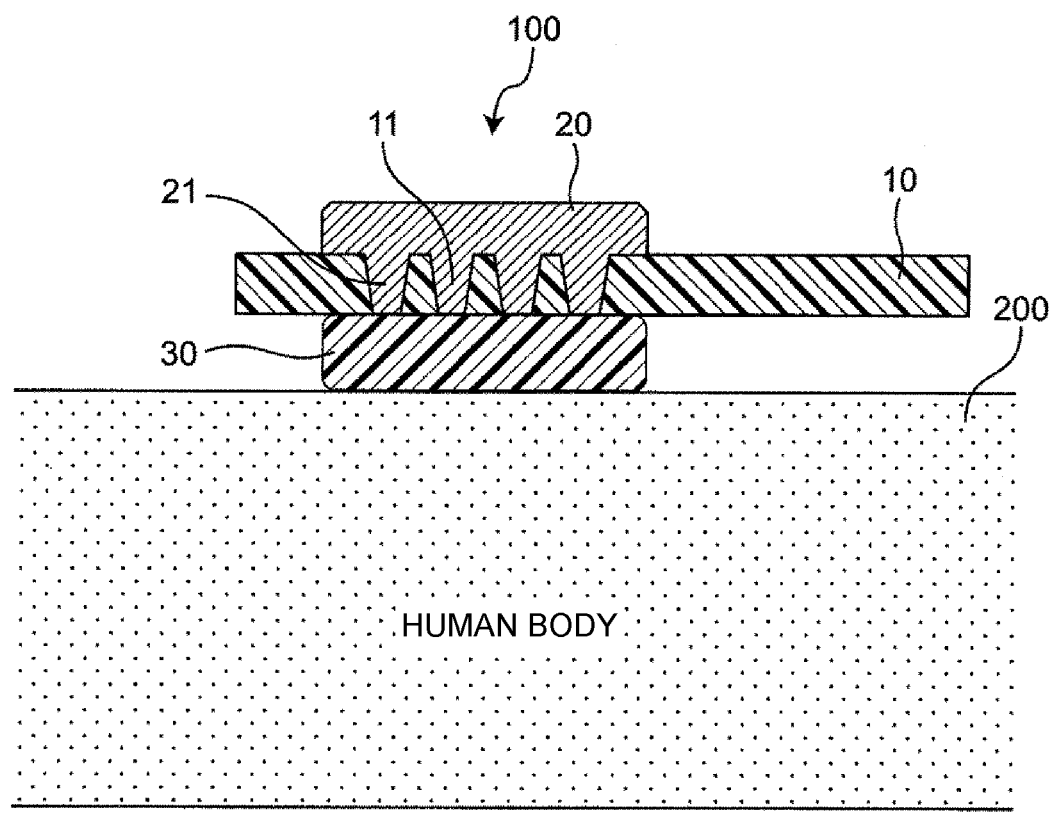
FIG. 3 is the cross-sectional view of a living body-attachable electrode.

FIG. 3 is the schematic diagram of the cross section of the living body-attachable electrode 100 which is used to describe the electric connection between the measuring electrode 20 and the gel electrode 30. The measuring electrodes 21a, 21b, 22a, and 22b are collectively referred to as the "measuring electrodes 20", and the gel electrodes 31a, 31b, 32a, and 32b are collectively referred to as the "gel electrodes 30". Each of the measuring electrodes 20 has the connection relationship illustrated in FIG. 3 with corresponding one of the gel electrodes 30.

As illustrated in FIG. 3, in the substrate 10, a plurality of vias 11 are formed for each of the measuring electrodes 20. The measuring electrodes 20 are formed not only on the surface of the substrate 10 but also in the vias 11 formed in the substrate 10. A part of the measuring electrode 20 formed in the via 11 in the substrate 10 is referred to as a "via electrode 21". The measuring electrode 20 disposed on the side of the first main surface 10a of the substrate 10 is electrically connected to the gel electrode 30 disposed on the side of the second main surface 10b via the via electrodes 21 formed in the substrate 10.

Figure 4:
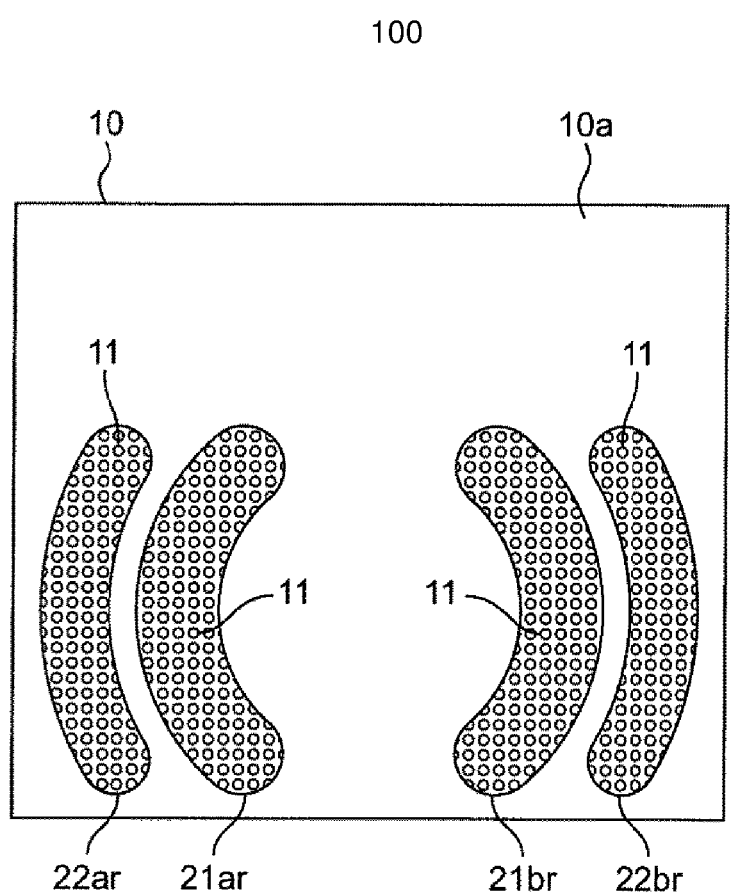
FIG. 4 is a diagram describing the arrangement of a plurality of vias in the substrate of a living body-attachable electrode.

FIG. 4 is a diagram describing the arrangement of vias formed in the substrate 10 in the living body-attachable electrode 100. As illustrated in FIG. 4, in the substrate 10, the vias 11 are formed in regions 21ar, 21br, 22ar, and 22br where the measuring electrodes 21a, 21b, 22a, and 22b are disposed, respectively.

The diameter of the single via 11 is set to a size that is very smaller than that of the electrodes 21a, 21b, 22a, and 22b. The flexibility in the arrangement of the vias 11 having the small diameter increases. The vias 11 can be arranged in accordance with various electrode shapes. That is, in the regions 21ar, 21br, 22ar, and 22br where the measuring electrodes 21a, 21b, 22a, and 22b are disposed, respectively, the vias 11 can be uniformly arranged. As a result, the shortest line of electric force can be realized between each of the measuring electrodes 21a, 21b, 22a, and 22b and corresponding one of the gel electrodes 31a, 31b, 32a, and 32b. The value of an interface resistance between the measuring electrode 20 and the gel electrode 30 can be reduced. Even if the electric connection between the gel electrode 30 and the via electrode 21 is locally broken because of the movement of a measurement target (for example, a human body), the increase in the interface resistance between the gel electrode 30 and the via electrode 21 can be minimized on condition that the many via electrodes 21 electrically connected to the gel electrode 30 remain.

The living body-attachable electrode 100 having the above configuration is used in such a manner that the gel electrodes 31a, 31b, 32a, and 32b are attached to a human body 200 that is a measurement target to be in contact with a part of the human body 200. In a state in which the living body-attachable electrode 100 is attached to the human body, a measurement current is applied from, for example, an external apparatus to the measuring electrodes 22a and 22b via the connector pad 50. The measurement current applied to the measuring electrodes 22a and 22b is applied to the human body 200 that is a measurement target via the via electrodes 21 and the gel electrodes 32a and 32b. At that time, a voltage applied to a measurement part is measured via the gel electrodes 31a and 31b, the via electrodes 21, and the measuring electrodes 21a and 21b. The voltage measured by the measuring electrodes 21a and 21b is transmitted to the external apparatus via the connector pad 50. The external apparatus can measure the resistance of the measurement target (human body) on the basis of the value of the measured voltage by the four-terminal sensing.

2. Manufacturing Process of Living Body-Attachable Electrode

FIGS. 5A-5D are diagrams describing the process of manufacturing the living body-attachable electrode 100. The manufacturing process of the living body-attachable electrode 100 will be described below.

Figure 5A:
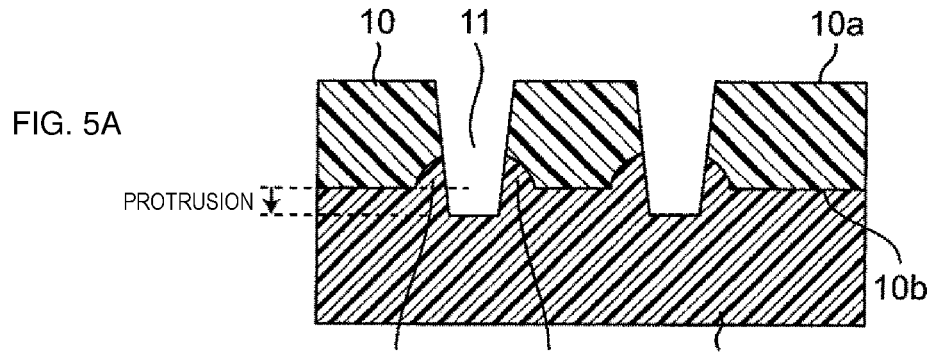
FIGS. 5A-5D are diagrams describing the manufacturing process of a living body-attachable electrode.

First, the substrate 10 having stretchability is laminated on a PET (polyethylene terephthalate) resin layer 80. Laser processing is performed upon the substrate 10 laminated on the PET resin layer 80, so that the vias 11 are formed in the substrate 10. Specifically, as illustrated in FIG. 5A, laser light is emitted from the side of the first main surface 10a of the substrate 10 to the substrate 10 to form the vias 11 in the substrate 10. For example, the vias 11 are formed such that the pitch therebetween is 0.5 mm and the diameter thereof is in the range of 0.15 to 0.30 mm.

Figure 5B:
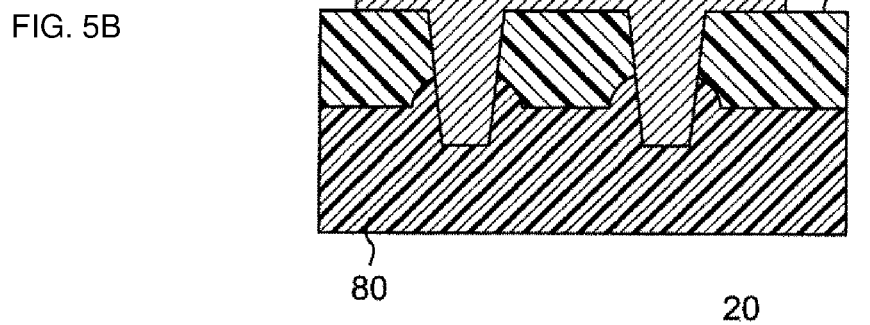
Figure 5C:
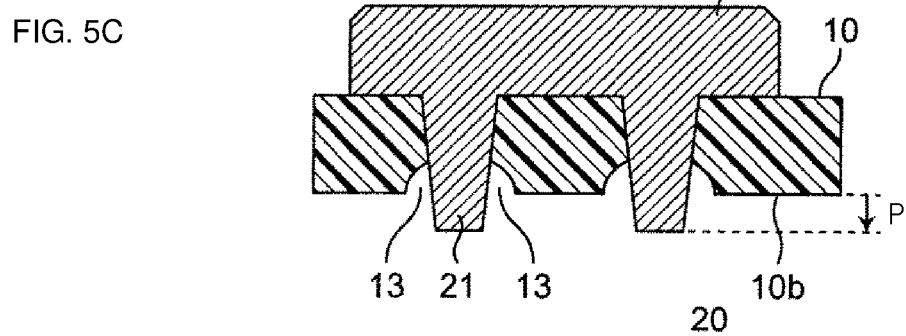

At that time, the depth of the via formed in the substrate 10 and the PET resin layer 80 is set such that the leading end portion of the completed via electrode 21 protrudes from the second main surface 10b of the substrate 10 as illustrated in FIGS. 5A and 5C. For example, the depth of the via is set such that the leading end portion of the via electrode 21 protrudes from the second main surface 10b of the substrate 10 by 0.01 mm or greater (for example, 0.02 mm). The adjustment of a laser output strength at the time of laser processing can make a half-cut hole that penetrates through only the substrate 10 and stops in the PET resin layer.

In the laser processing, a burr 82 is formed around a hole formed in the PET resin layer 80. The burr 82 forms a depression portion around the via 11 at the second main surface 10b of the substrate 10 as will be described below.

Upon the completion of the vias 11 in the regions 21ar, 21br, 22ar, and 22br where the respective measuring electrodes 20 are formed, a conductive material is filled into the vias 11 as illustrated in FIG. 5B to form the via electrodes 21. Consequently, the measuring electrodes 20 are formed on the substrate 10. As the conductive material, for example, the mixture of metal powder made of silver or copper and an elastomer resin such as silicone is used.

Figure 5D:
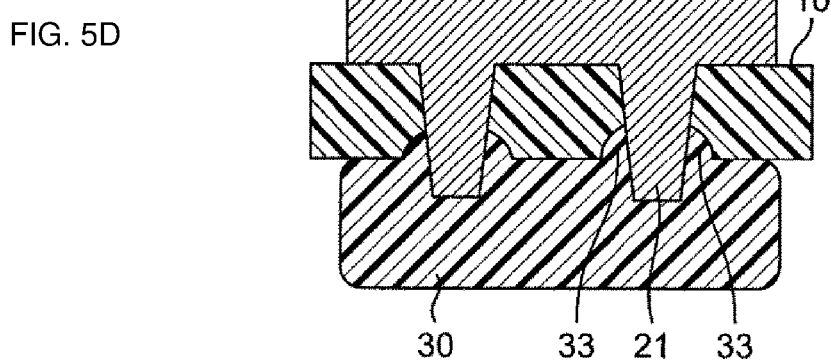

Subsequently, as illustrated in FIG. 5C, the PET resin layer 80 is separated from the substrate 10. In this state, depression portions 13 are formed around the opening portions of the vias 11 at the second main surface 10b of the substrate 10. A conductive gel is provided on the second main surface 10b of the substrate 10 to form the gel electrodes 30 as illustrated in FIG. 5D. At that time, using the depression portion 13 of the substrate 10, a ring projection portion 33 of the gel electrode 30 is formed around the via electrode 21. The formation of the projection portion 33 increases the area of a contact between the via electrode 21 and the gel electrode 30. This leads to the improvement of measurement accuracy.

The portion of the via electrode 21 protruding from the second main surface 10b of the substrate 10 is buried in the gel electrode 30. Burying the leading end of the via electrode 21 in the gel electrode 30 has an anchor effect upon the via electrode 21. All of the measuring electrodes 20, the substrate 10, and the gel electrodes 30 have stretchability. When the gel electrode 30 in the lowest layer expands with the movement (expansion and contraction) of a part of a human body to which the living body-attachable electrode 100 is attached, a shearing force generated between the gel electrode 30 and the substrate 10 is suppressed because the via electrode 21 harder than the gel electrode 30 is buried in the gel electrode 30. As a result, at the time of the expansion and contraction of the living body-attachable electrode 100, the gel electrode 30 and the substrate 10 are less likely to separate from each other. It has been confirmed by measurement performed by the inventor and the like that the degree of suppression of a shearing force increases with the increase in the degree of protrusion of the via electrode 21.

Through the above process, the living body-attachable electrode 100 according to this embodiment can be manufactured.

3. Variations in Electrode Shape

Figure 6A:
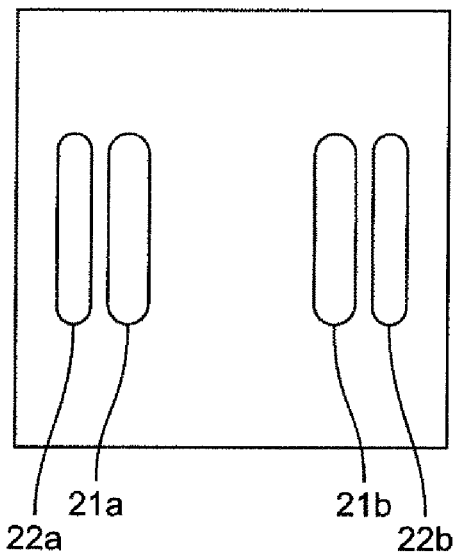
FIGS. 6A and 6B are diagrams describing variations in the shape of a measuring electrode in a living body-attachable electrode.
Figure 6B:
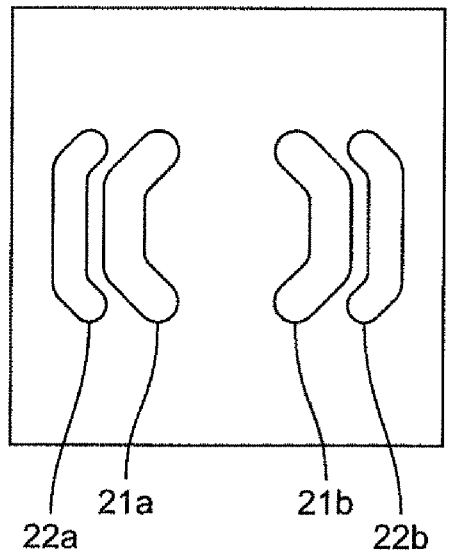

The measuring electrodes 20 having the arc shape have been described above (see, for example, FIG. 1). However, the shape of the measuring electrodes 20 (and the gel electrodes 30) is not limited to the arc shape. FIGS. 6A and 6B are diagrams describing the variations in the shape of the measuring electrodes 20 (and the gel electrodes 30). As illustrated in FIG. 6A, the measuring electrodes 20 may have a linear shape. Alternatively, as illustrated in FIG. 6B, the measuring electrodes 20 may have a shape (hereinafter referred to as a "bracket shape") in which the center portion thereof linearly extends and both leading end portions thereof linearly bend in the same direction. The measuring electrodes 20 may have a curve shape in which both leading end portions thereof curve in the same direction. In this case, the leading ends of the two opposite measuring electrodes 21a and 21b or the two opposite measuring electrodes 22a and 22b in the longitudinal direction inwardly bend to be closer to each other.

4. Rounded Corner of Leading End Portion of Measuring Electrode

Figure 7:
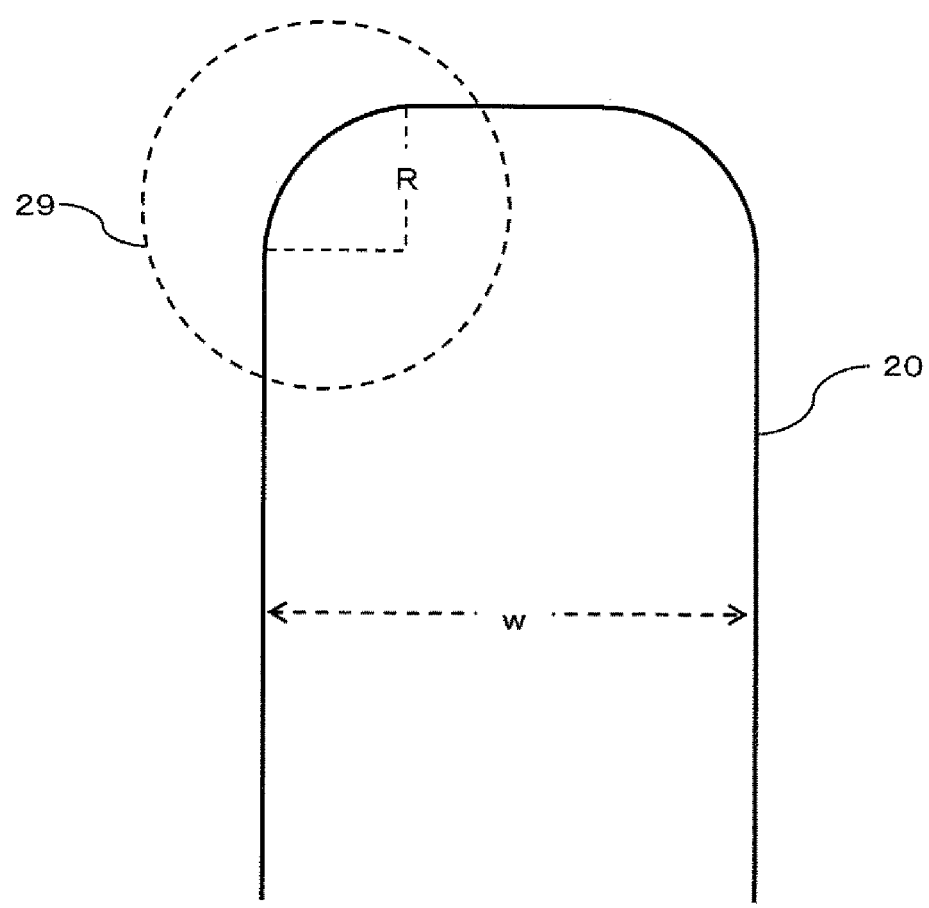
FIG. 7 is a diagram describing a rounded corner (R) of a leading end portion of a measuring electrode.

In this embodiment, as illustrated in FIG. 7, the measuring electrode 20 has a rounded corner portion 29 at the leading end thereof. By allowing the electrode to have the rounded corner portion 29 at the leading end of the electrode, the stress generated by the expansion and contraction of the living body-attachable electrode 100 in an oblique direction (the intermediate direction between the X direction and the Y direction) can be suppressed. In addition, the area of a region where the measuring electrode is disposed can be reduced.

Figures 8A, 8B:
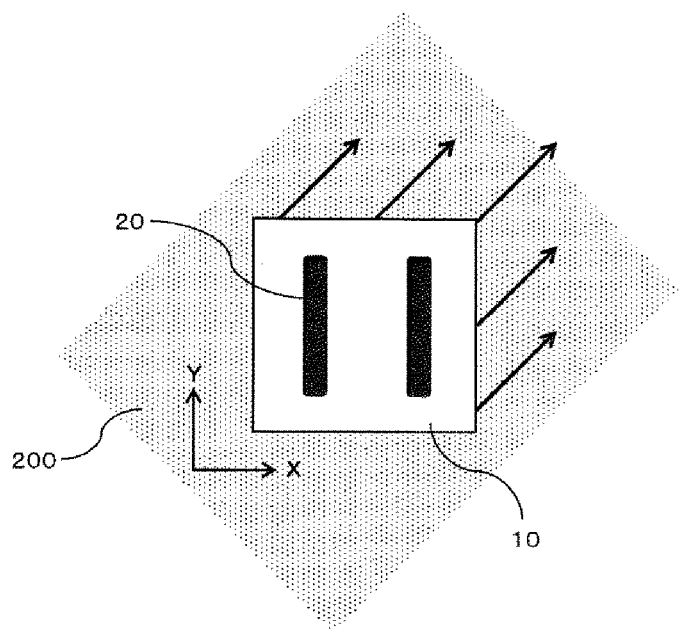
FIGS. 8A and 8B are diagrams describing the relationship between the rounded corner (R) of a measuring electrode and the maximum stress.

In this embodiment, the rounded corner portion 29 at the leading end portion of the measuring electrodes 20, that is, a curvature radius R, is set to 2 mm or greater and w/2 mm or less (w represents the width of the measuring electrode 20). FIG. 8B is a diagram illustrating the results of measurement of the maximum stress generated by the expansion and contraction of the living body-attachable electrode 100 in the oblique direction illustrated in FIG. 8A in the case of three types of curvature radii R. As is apparent from the drawing, the larger the curvature radius R, the smaller the value of the maximum stress. However, if R is greater than w/2, the end portion will be sharpened. From a practical standpoint, the upper limit of R is considered to be w/2.

From a practical standpoint, it is desirable that the lower limit of R be 2 mm. A measuring electrode having an optional shape can have a rounded corner at the leading end thereof. It is desirable that the measuring electrodes 21a and 21b have the same w and the measuring electrodes 22a and 22b have the same w. The w of the measuring electrodes 21a and 21b and the w of the measuring electrodes 22a and 22b may be different. In this case, the curvature radius R is set for the w of each of the measuring electrodes 20.

5. Various Measurement Results

The inventor and the like measured stresses generated because of the expansion and contraction of the living body-attachable electrode 100 in the case of some shapes of the measuring electrode 20. Specifically, the inventor performed measurement in the case of three types of shapes, the linear shape illustrated in FIG. 6A, the bracket shape illustrated in FIG. 6B, and the arc shape illustrated in FIG. 1, 2, and other drawings.

Figure 9:
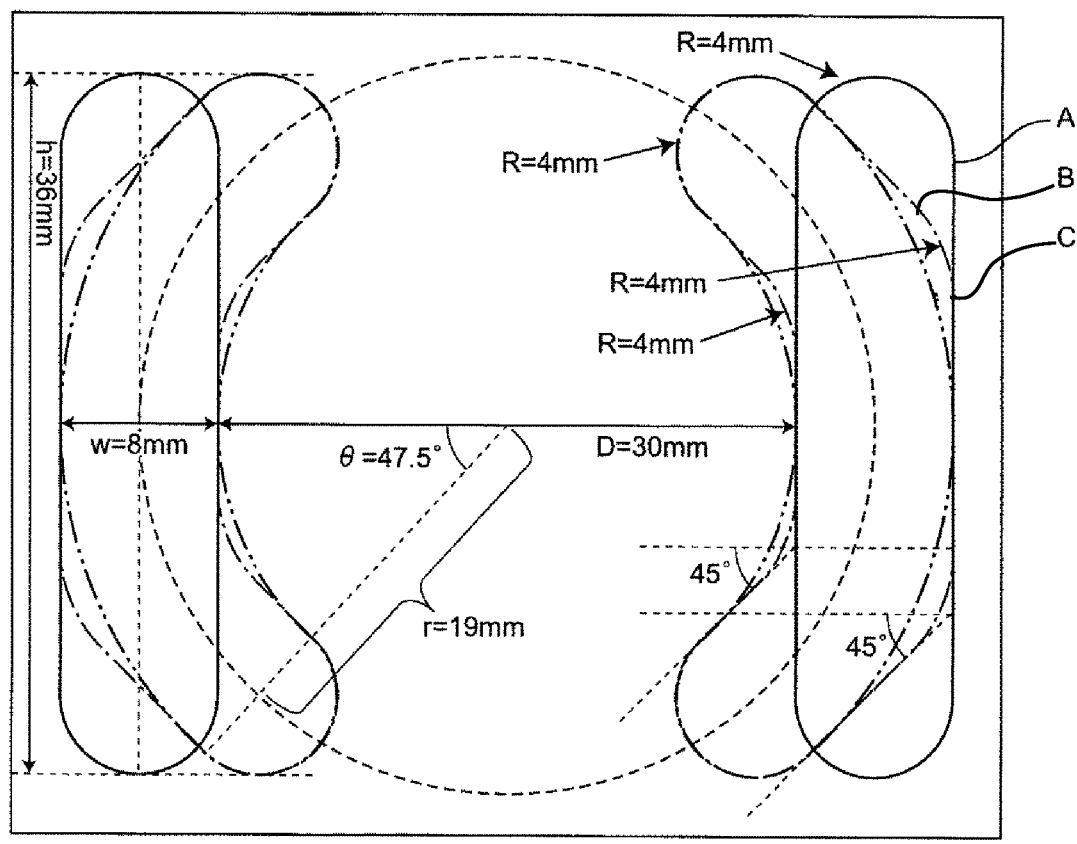
FIG. 9 is a diagram describing various dimensions for measuring electrodes used in measurement and simulations.

FIG. 9 is a diagram illustrating various dimensions for the measuring electrodes of the respective shapes used in measurement. Measurement was performed under the conditions illustrated in FIG. 9. FIG. 10 illustrates stress measurement results corresponding to the measuring electrodes of the respective shapes.

Measurement was performed in the case of three electrode shapes illustrated in FIG. 9, a linear shape A, an arc shape C (the radius of 19 mm, the width of 8 mm, and the angle of 95°), and a bracket shape B that is an intermediate shape between them (the shape inwardly protruding at an angle of 45° while retaining h=36 mm). The values of the maximum stress generated because of expansion and contraction in the Y direction, the X direction, and the oblique direction in the case of the respective shapes were obtained by measurement.

In the comparison between the linear shape and the bracket shape with reference to FIG. 10, the larger degree of suppression of the stress value is obtained in some directions (the Y direction and the oblique direction) in the case of the bracket shape. In the comparison between the bracket shape and the arc shape, the larger degree of suppression of the stress value is obtained in the case of the arc shape. It can be considered that the effect of the stress suppression becomes larger as the shape approaches the arc shape.

Figure 11A:
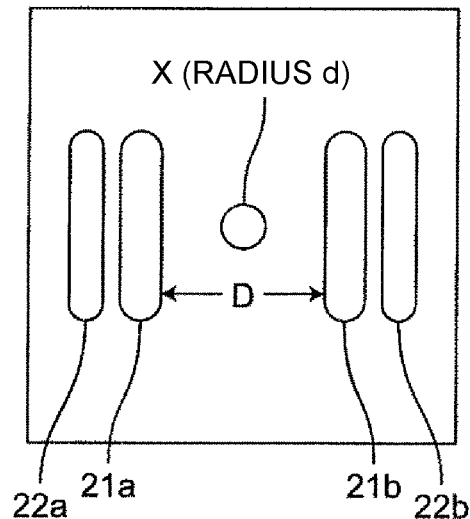
FIGS. 11A-11C are diagrams describing conditions under which the simulations of the change in a potential difference caused by the inclusion of a foreign body are performed.
Figure 11B:
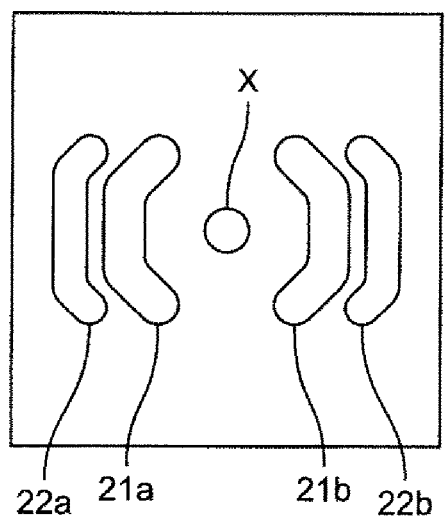
Figure 11C:
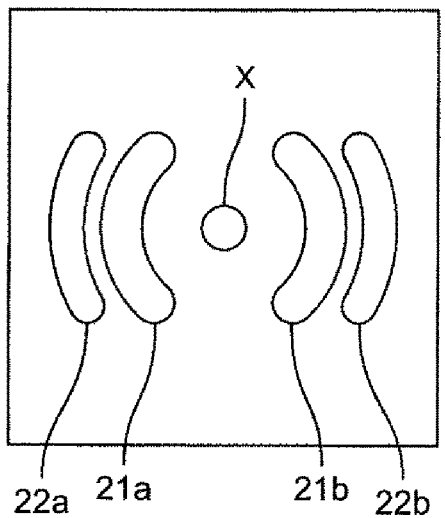
Figure 12:
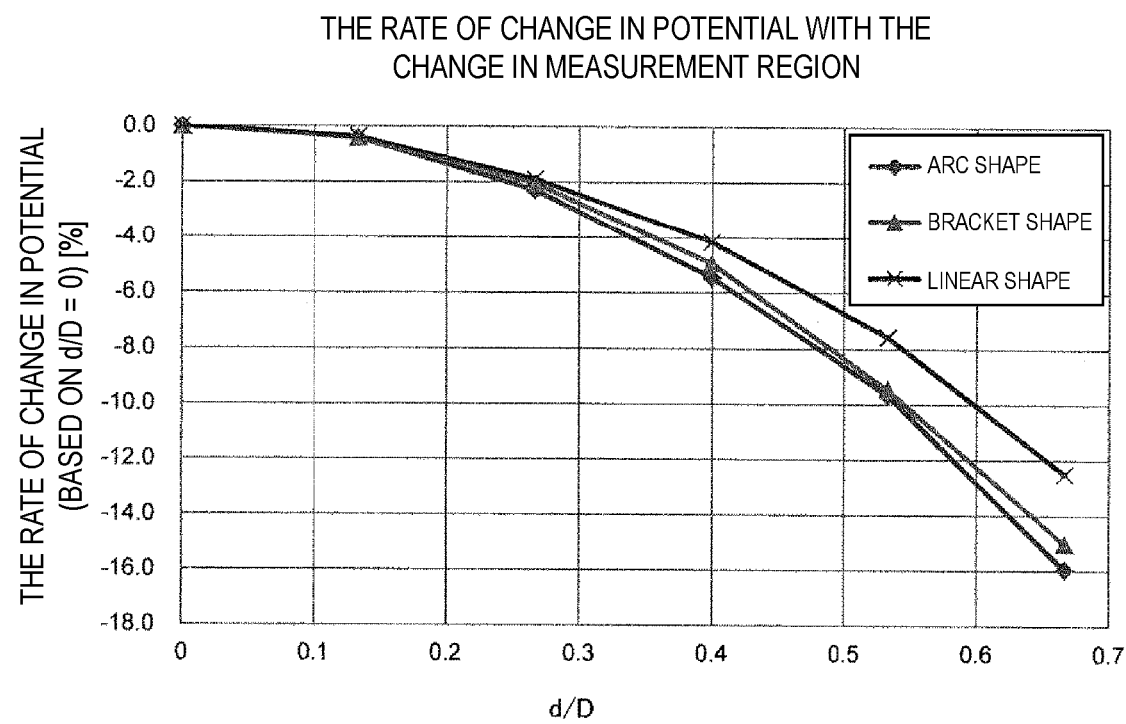
FIG. 12 is a diagram illustrating the results of the simulations of the change in a potential difference caused by the inclusion of a foreign body.

The change in the potential difference that occurs because of the mixture of a foreign body at a measurement point was simulated using measuring electrodes of the respective shapes. Specifically, assuming that a circle measurement point X having a radius d placed between opposite electrodes was a foreign body (having a resistance value less than that of a skin) as illustrated in FIGS. 11A-11C, the change in the potential difference that occurs because of the mixture of the foreign body was simulated using the measuring electrodes of the respective shapes. FIG. 12 illustrates the result of the simulation. In the graph illustrated in FIG. 12, the vertical axis represents a potential difference change rate ΔV/V (based on d/D=0) calculated from a potential difference V generated at the measuring electrode of each shape and the horizontal axis represents d/D.

As is apparent from the graph in FIG. 12, the change rate increases in the order of the linear shape, the bracket shape, and the arc shape. It can be considered that the effect of the improvement of measurement accuracy increases in this order. Although not illustrated, it was observed that a current density near the measurement point at the center was higher in the case of the bracket shape or the arc shape whose leading end is inwardly directed as compared with the linear shape and a potential change became larger in response to a resistance change caused by the same foreign body.

6. Conclusion of Embodiment

As described above, the living body-attachable electrode 100 according to this embodiment includes the substrate 10 that has the first main surface 10a and the second main surface 10b and is made of a material having stretchability, a first electrode pair that is formed on/in the first main surface 10a and includes the two opposite electrodes 21a and 21b used for the measurement of a voltage, a second electrode pair that is formed on/in the first main surface 10a and includes the two opposite electrode 22a and 22b used for the application of a current which sandwich the first electrode pair, and the gel electrodes 31a, 31b, 32a, and 32b that are formed on the second main surface 10b and are in a one-to-one correspondence with the electrodes in the first and second electrode pairs. Each of the electrodes 21a, 21b, 22a, and 22b (20) and corresponding one of the gel electrodes 31a, 31b, 32a, and 32b are electrically connected to each other via the via electrode 21 (via conductors) penetrating through the substrate 10.

With the above configuration, there can be provided a living body-attachable electrode with which the burden to a human body is suppressed when the living body-attachable electrode is attached to the human body (an example of a living body) and high measurement accuracy is realized.

In the living body-attachable electrode 100, each of the electrodes in the first and second electrode pairs may include an end portion having a rounded corner portion (see FIG. 7). The stress generated at the time of the expansion and contraction of the substrate 10 in the living body-attachable electrode can therefore be suppressed.

The corner portion of the end portion of each of the electrodes has a curvature radius R that is greater than or equal to 2 mm and less than or equal to w/2 where w represents a width of each of the measuring electrodes 20. By setting the curvature radius in this range, the stress generated at the time of the expansion and contraction of the living body-attachable electrode 100 can be practically and effectively suppressed.

Each of the measuring electrodes 20 may include a leading end portion that bends toward the opposite electrode in a straight or curved manner (see FIGS. 2A and 6(B)). By inwardly directing the leading end portions of the opposite electrodes, the area of a region where the measuring electrodes are disposed can be reduced. As a result, the stress generated at the time of the expansion and contraction of the living body-attachable electrode 100 can be suppressed.

Specifically, each of the electrodes 20 may have an arc shape. The arc shape can realize the further suppression of a stress illustrated in FIG. 10 and the further improvement of measurement accuracy illustrated in FIG. 12.

The electrodes 20 may be concentrically arranged (see FIG. 2B). With this configuration, the suppression of a stress and the improvement of measurement accuracy can be realized.

A part of the via electrode 21 may protrude from the substrate 10 and be buried in the gel electrode 30 (see FIG. 5D). With this configuration, a shearing force generated between the substrate 10 and the gel electrode 30 can be suppressed.

The projection portion 33 of the gel electrode 30 may be provided around the via electrode 21. With this configuration, the area of a contact between the via electrode 21 and the gel electrode 30 can be increased. This leads to the improvement of measurement accuracy.

The lead wiring line 25 may be connected to each of the measuring electrodes 20. The lead wiring lines 25 may be arranged symmetrically about a reference line connecting midpoints between a pair of the opposite electrodes. With this configuration, noises generated between the connector pad 50 and the respective via electrodes 21 are likely to be equal. The calibration at the subsequent stage can therefore be easily performed.

Each of the measuring electrodes 20 and corresponding one of the gel electrodes 30 may have the same shape. As a result, measurement accuracy can be improved.

In the above embodiment, as the configuration (number, arrangement, shape, and the like) of the measuring electrode 20 in the living body-attachable electrode 100, a configuration suitable for the measurement of a resistance value by the four-terminal sensing has been described. However, this configuration (number, arrangement, shape, and the like) of the measuring electrode does not necessarily have to be used, and may be changed as appropriate in accordance with the use or purpose. The material and size of the substrate, the measuring electrodes, and the like are illustrative, and are not limited to the above material and size.

The above embodiment is provided to illustrate the embodiment of the present disclosure. It should be noted that various changes, replacements, additions, omissions, and the like may be applied to the above embodiment within the scope of the claims or equivalents thereof.

REFERENCE SIGNS LIST 10 substrate
11 via
13 depression portion
10a first main surface of substrate
10b second main surface of substrate
20 measuring electrode
21 via electrode
25 lead wiring line
21a and 21b measuring electrode for measurement of voltage
22a and 22b measuring electrode for application of current
30, 31a, 31b, 32a, and 32b gel electrode
50 connector pad
80 PET resin layer
100 living body-attachable electrode
200 human body

The invention claimed is:

1. A living body-attachable electrode comprising:
a substrate comprising a first main surface and a second main surface, the substrate being of a stretchable material;
a first electrode pair that is on the first main surface or in the substrate, and that comprises two opposing electrodes;
a second electrode pair that is on the first main surface or in the substrate, and that comprises two opposing electrodes that sandwich the first electrode pair; and
a plurality of gel electrodes on the second main surface mirroring the electrodes of the first and second electrode pairs,
wherein each electrode of the first and second electrode pairs is electrically connected to a corresponding one of the plurality of gel electrodes by a via conductor through the substrate.

2. The living body-attachable electrode according to claim 1, wherein each electrode of the first and second electrode pairs has at least one rounded corner.

3. The living body-attachable electrode according to claim 2, wherein the rounded corner of each electrode of the first and second electrode pairs has a curvature radius R that is greater than or equal to 2 mm and that is less than or equal to half of a width of the electrode.

4. The living body-attachable electrode according to claim 1, wherein each electrode of the first and second electrode pairs has a leading end that is bent toward the opposing electrode of the electrode pair.

5. The living body-attachable electrode according to claim 4, wherein each electrode of the first and second electrode pairs has an arc shape.

6. The living body-attachable electrode according to claim 5, wherein the electrodes of the first and second electrode pairs are arranged concentrically.

7. The living body-attachable electrode according to claim 1, wherein a part of the via conductor protrudes through the second main surface of the substrate and is buried in the corresponding gel electrode.

8. The living body-attachable electrode according to claim 1, wherein at least one gel electrode is projected into a depression of the substrate around the corresponding via conductor.

9. The living body-attachable electrode according to claim 1, further comprising:
a plurality of lead wiring lines each connected to a corresponding one of the electrodes of the first and second electrode pairs,
wherein the lead wiring lines are arranged symmetrically about a center line of the substrate that extends between the electrodes of each of the first and second electrode pairs.

10. The living body-attachable electrode according to claim 1, wherein at least one of the electrodes of the first and second electrode pairs and the corresponding one of the gel electrodes have the same shape.

* * * * *